United States Patent [19]

Weissman

[11] Patent Number: 4,661,069
[45] Date of Patent: Apr. 28, 1987

[54] DEVICE FOR RETAINING A REMOVABLE DENTAL PROSTHESIS

[76] Inventor: Bernard Weissman, 225 E. 48th St., New York, N.Y. 10017

[21] Appl. No.: 778,861

[22] Filed: Sep. 23, 1985

[51] Int. Cl.⁴ ............................................. A61C 13/22
[52] U.S. Cl. ................................................... 433/183
[58] Field of Search ......................... 633/181, 182, 183

[56] References Cited

FOREIGN PATENT DOCUMENTS 640687  7/1950  United Kingdom ................. 433/183

Primary Examiner—Robert Peshock
Attorney, Agent, or Firm—Goodman & Teitelbaum

[57] ABSTRACT

A retaining device for removably securing a dental prosthesis in position. The retaining device includes a male section which can be secured to the side of a fixed tooth and a cooperating female section which can be secured within the dental prosthesis. The male section includes a projection which is received in an inverted U-shaped housing at the forward end of the female section. A channel member upwardly extending from the housing provides a keyway for receiving a key upwardly extending from the projection, to maintain a secure stability between the male and female sections. A spring loaded plunger member positioned within the female section extends into the housing and engages a recess formed in the projection, thereby locking the two sections together.

16 Claims, 6 Drawing Figures

DEVICE FOR RETAINING A REMOVABLE DENTAL PROSTHESIS

BACKGROUND OF THE INVENTION

This invention relates to a device for retaining a removable dental prosthesis, and more particularly to a device for securing a removable dental prosthesis to existing fixed dentition.

During the course of various dental procedures, a dental prosthesis may be installed in the mouth which is secured onto adjacent fixed dentition. Such dental prosthesis is arranged so that it can be secured to the fixed dentition, where it is removable under various conditions. For example, partial dentures and removable bridge work are inserted in place in the mouth and must be held secure. However, for cleaning and maintenance, they must be removable.

Numerous devices have been provided for this purpose, all of which provide both the fixed and removable features. However, the critical aspect of such devices is to retain the dental prosthesis secured in position during actual use so as to avoid all types of rotation, lateral movement, and displacement of the removable dentition from its proper position in the mouth. Any such movement or displacement may cause a disturbance and annoyance to the patient during normal use.

If the retaining device permits such displacement, there can result a bending or breakage of the dental prosthesis and likewise can chip or cause damage, in other ways, to the fixed dentition to which the dental prosthesis is connected. Furthermore, any rotation and/or movement causes an uncertainty to the user, and the user may get the feeling that the dental prosthesis may fall out, slip, slide or cause embarrassment. In this way, the user never feels secure with his dental prosthesis unless it is adequately retained onto the fixed dentition without displacement thereof.

U.S. Pat. No. 4,348,181 describes a retaining device for removably securing a dental prosthesis in position. The retaining device includes a male section for securement to the side of the fixed tooth and a cooperating female section for securement within the dental prosthesis. The male section includes a projection which is received in an inverted U-shaped housing at the forward end of the female section. A spring loaded plunger member positioned within the female section projects from the housing and engages in a recess provided in the male projection thereby locking the two sections together.

With the male member permanently fixed in the fixed dentition, the dental prosthesis having the female section secured therein can be downwardly inserted so that the U-shaped housing fits over the male projection and engages onto it. The plunger locks into the recess in the male projection to secure the dental prothesis in place.

While such retaining device has been found most useful, occasionally there occurs some rotation or lateral movement between the male and female sections. Although the dental prosthesis will nevertheless be retained in place, such rotational or lateral movement between the male and female sections cause slight displacements of the dental prosthesis causing an insecurity in the user, and can cause damage or breakage of the dental prosthesis or dentition.

Accordingly, while such retaining device has been found to be most innovative and novel over all of the prior art, further improvements in such retaining device is warranted in order to obtain additional security and stability between the male and female sections to avoid any possible movement or displacement therebetween.

SUMMARY OF THE INVENTION

Accordingly, it is an object of the present invention to provide an improved device for retaining a removable dental prosthesis in the mouth.

A further object of the present invention is to provide securing means for a removable dental prothesis which makes the interconnection of the prothesis more secure than heretofore obtainable.

Another object of the present invention is to provide a retaining device for a removable dental prosthesis which prevents possible lateral movement or rotation between the dental prosthesis and the fixed dentition to which it is secured.

Still another object of the present invention is to provide a retaining device for removably securing a dental prothesis which facilitates securement of the dental prosthesis in place in order to insure proper connection of the dental prosthesis to the fixed dentition.

Yet a further object of the present invention is to provide a retaining device for securing a dental prothesis which permits easy insertion of the device into the removable prosthesis and the fixed teeth, to assure suitable alignment and appropriate interconnection of the sections of the retaining device.

A further object of the present invention is to provide a retaining device for a removable dental prothesis which includes male and female sections which can engage each other, and includes appropriate guides which coact between the male and female sections to maintain stability between them to prevent rotational and lateral movement relative thereto, as well as providing a longer path of engagement therebetween.

Briefly, in accordance with the present invention, there is provided a retaining device for removably securing a dental prosthesis in position. The device includes a first section which can be secured to a fixed tooth. A projection extends from the first section. A second section is provided which can be secured in the dental prosthesis. A housing extends from the second section for receiving the projection. The first and second sections are appropriately shaped to prevent relative rotation between them.

There is further provided a guide mechanism having cooperating parts which respectively extend from the housing and the projection, and coact with each other in order to maintain stability between the first and second sections, and to provide a longer path of engagement therebetween. The guide mechanism includes a channel upstanding from the housing, and having an internal longitudinal keyway. The guide mechanism also includes an elongated plug member upstanding from the projection in the shape of a mating key which can be received in the keyway. The keyway communicates with the housing so that the housing can be placed over the key and slid downwardly, whereby the key is then slidably received within the keyway as the housing fits over the projection. The key remains in the keyway providing stability between the first and second sections to avoid rotation and lateral movement therebetween.

BRIEF DESCRIPTION OF THE DRAWINGS

With the above and additional objects and advantages in view, as will hereinafter appear, this invention comprises the devices, combinations, and arrangements of parts hereinafter described by way of example and illustrated in the accompanying drawings of a preferred embodiment in which.

In the various figures of the drawings, like reference characters designate like parts.

DETAILED DESCRIPTION OF THE PREFERRED EMBODIMENT

Figure 1:
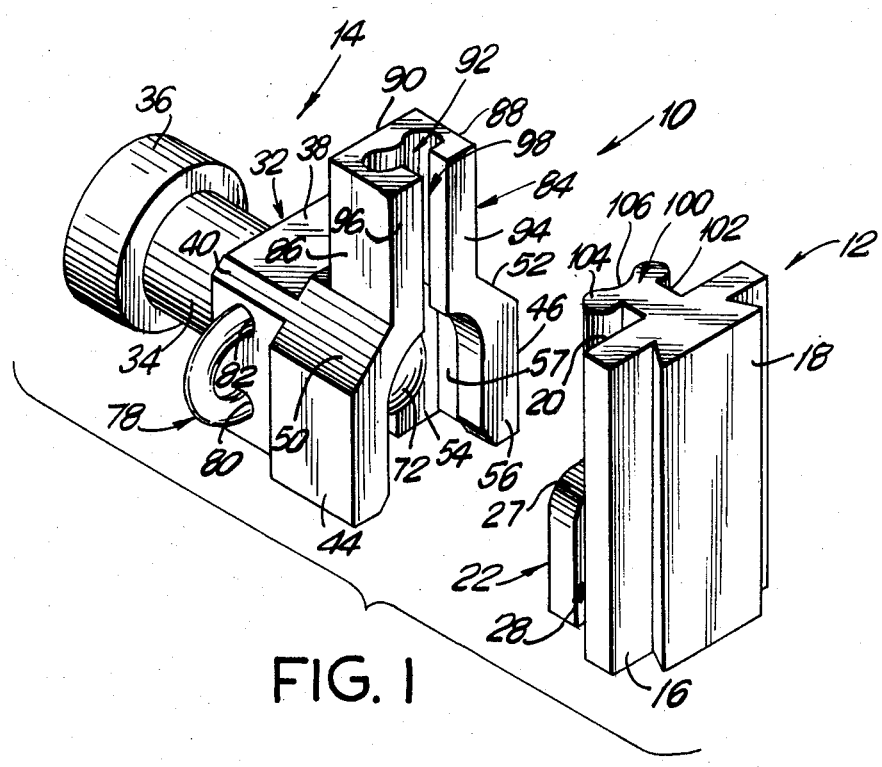
FIG. 1 is a perspective view of the male and female sections of the retaining device, unassembled, in accordance with the present invention.
Figure 2:
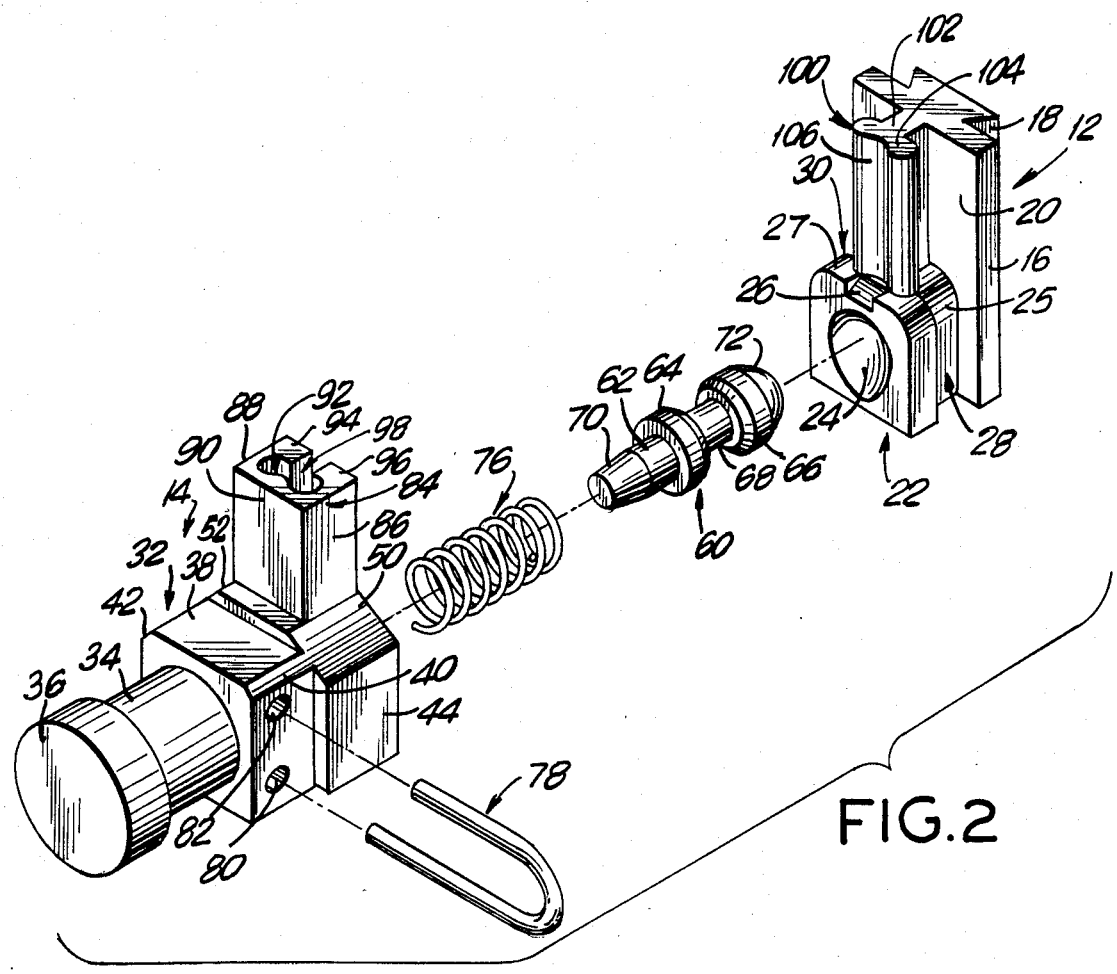
FIG. 2 is an exploded perspective view of the various parts forming the retaining device shown in FIG. 1.
Figure 3:
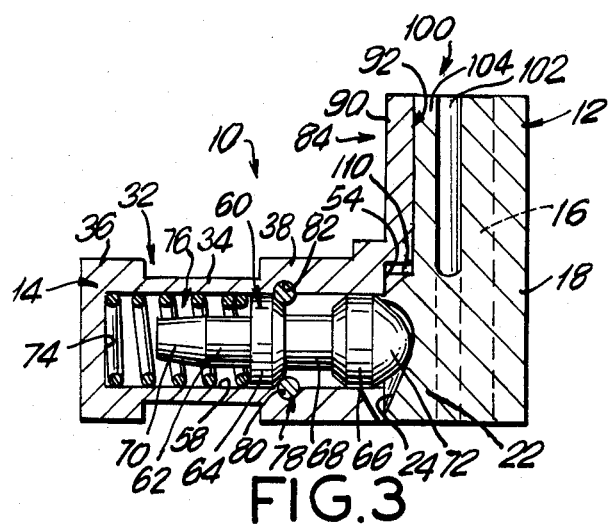
FIG. 3 is an elevational sectional view taken through the retaining device when the male and female sections thereof are in an assembled, engaged position.

Referring now to FIGS. 1-3, the retaining device is shown generally at 10 and comprises a fixed male section 12 which is to be secured to the side of a fixed tooth, and a cooperating free female section 14 to be secured in the dental prosthesis. The male section 12 includes a solid rectangular plate 16 from which extends toward the rear a dovetail spline 18. The height of the spline 18 extends the entire height of the plate 16. Protruding from the front face 20 of the plate 16, and extending only from the lower half thereof, is a projecting block 22 which constitutes a recessed member, the block 22 having a narrower width than the plate 16. Formed into the projecting block 22 is a recess 24, and above the recess 24 is provided a cam surface 26 formed as a cut out at the upper edge of the block 22. The upper edge and sides of the block 22 are tapered or curved to provide curved surfaces 25, 27. On either side of the block 22 there is provided undercut channels 28, 30 for receiving a portion of the female section 14, as will hereinafter be explained.

The female section 14 includes a casing shown generally at 32 which is formed of various sections including a cylindrical section 34 from which extends an enlarged circular flange at its base 36. Forward of the cylindrical section 34 is a block section 38 having tapered or beveled surfaces 40, 42 at is upper corners. At the front of the casing there is provided a larger section which is provided with a substantially inverted U-shaped portion including the side sections 44, 46. The side sections 44 and 46 have their upper ends tapered or beveled at 50 and 52. It should be noted that the front portion is hollow and includes an open bottom. The front facing 54 within the hollow of the front portion is spaced from the outer front face 56 of the female section 14, with the side walls of the hollow being undercut at 57 adjacent to the front facing 54, as can best be seen in FIG. 1.

As is noted in FIG. 3, a longitudinal bore 58 extends from the front facing 54 of the female section 14 inwardly through the various sections of the casing 32 and into the rear collar section or base 36. Positioned within the bore 58 is a plunger member, shown generally at 60. The plunger member 60 includes a cylindrical body section 62 along which is positioned two enlarged circular collar sections 64, 66, spaced apart from each other to define a neck section 68 therebetween. It should be noted that the collar sections have beveled edges facing toward the intermediate neck section 68. The rear 70 of the body section 62 is slightly tapered. Forward of the collar 66 is a front end having a conical projection 72.

A coil spring 76, having closed end loops at both ends thereof, is mounted into the rear of the bore 58 and extends between the back end 74 of the bore 58 and the first collar 64 of the plunger member 60. The body portion 62 of the plunger member together with the tapered rear section 70, extend into the center of the coil spring 76.

The plunger member 60 is held in place within the case by means of a U-shaped wire clip or brad 78 which is inserted into the spaced apart receiving holes 80, 82 which extend through the section 38 so that the holes extend into the bore 58. The spacing between the holes 80, 82 is less than the diameter of the bore 58 so that the legs of the wire clip 78 extend into the bore 58 and are disposed around the neck portion 68 of the plunger member. The plunger member 60 is thus captured within the casing 32 but is free to axially move within the bore 58 a distance corresponding to the length of the neck section 68. The collars 64, 66 will abut against the legs of the wire clip 78, thus defining the limit of the axial movement of the plunger member. The length of the plunger member is such that it extends forward of the casing facing 54 and into the space defined by the inverted U-shaped portion at the front of the casing 32.

When assembled as shown in FIG. 3, the projecting block 22, extending forward of the plate 16 of the male section 12, is received within the inverted U-shaped portion at the front of the casing 32, with the undercuts 28, 30 of the block 22 and the undercuts 57 within the hollow of the block and the undercuts 57 within the hollow of the casing 32 providing a tongue and groove engagement to substantially prevent relative rotation therebetween. The plunger member extends into the recess 24 formed in the projecting block to secure the sections 12 and 14 together.

Upwardly extending from the upper end of the forward larger section of the casing 32 is a channel member 84. The channel member 84 includes side walls 86 and 88, and a rear wall 90. The side walls 86, 88 continue upwardly from the beveled sides 50, 52 at the upper ends of the side sections 44, 46. The depth of the channel member 84 from the outer front face 56 is less than the length of the side sections 44, 46 of the casing 32 so as to form a rear stepped portion therebetween at the rear wall 90, as best shown in FIG. 2.

Internally of the channel member 84, there is formed a longitudinal keyway 92 which communicates with the open hollow interior formed in the front portion of the casing 32. The front wall of the channel member 84 is formed by a pair of opposing front wall sections 94, 96 providing an open mouth or space 98 therebetween which communicates with the longitudinal keyway 92 and forms a part thereof. The mouth or space 98 continues downwardly to communicate with the U-shaped opening at the front of the casing 32. It should be noted, that the front wall sections 94, 96 are continuations of the lower front face 56 so as to lie in a common plane.

Accordingly, projecting forward from the front face 20 of the plate 16 of the male section 12, there is provided a longitudinal key 100 having a substantially T-shaped cross section corresponding to the combined shape of the keyway 92 and the mouth 98. Specifically, the key 100 extends upwardly from the projection 22. The key 100 includes a stem portion 102 which perpendicularly projects from the plate 16 and terminates in a substantially transverse wall section 104. The width of the wall section 104 is slightly less than the width of the keyway 92 in the channel member 84 so as to be slidably received therein. Likewise, the thickness of the stem portion 102 is less than the opening of the mouth 98 so as to be received therein.

The front face of the key 100 includes an elongated concave groove 106 which terminates at its bottom end proximate the cam surface 26. This groove 106 serves as a guideway for the conical tip 72 of the plunger 60 to slide along the groove 106 and be directed towards the cam surface 26 which guides the conical tip 72 into the recess 24 in the projection 22.

The parts are arranged so that the male section 12 can initially be secured to the side of a fixed tooth, and the female section 14 will then be inserted into the dental prothesis. The two sections 12 and 14 are first located so that they are adjacent to each other and then the dental prosthesis carrying the female section 14 is vertically moved downward into position. The lower housing at the front of the casing 32 will first be positioned onto the T-shaped key 100 with the front face 56 of the casing 32 positioned against the front face 20 of the plate 16. The wall section 104 will then be received into the keyway 92 of the channel member 84, with the stem portion 102 being received into the mouth 98, as the casing 32 is moved downwardly. The lower housing at the front of the casing 32 will finally move onto the projecting block 22, being guided by the arcuate surfaces 25 and 27, to position the projecting block 22 within the inverted U-shaped housing with the above mentioned tongue and groove engagement therebetween.

At the same time, upon initial engagement between the sections 12 and 14, the plunger member 60 is first guided into the longitudinal groove 106 along the key 100. The plunger will then be guided along the engagement path of this groove 106 and be directed onto the cam surface 26, and finally into the recess 24 provided in the projecting block 22. The assembled parts can be seen best in FIG. 3.

It should be noted in FIG. 3, that the projecting block 22 on the male section 12 is situated within the inverted U-shaped housing of the female section 14, the plunger member 60 is situated within the recess 24 and the key 100 is in keyway 92 of the channel member 84. The spring 76, biasing the plunger member, holds the plunger member tightly within the recess 24 and locks the projecting block 22 within the housing of the female section 14. Accordingly, a secure locking arrangement is provided. However, it should also be noted that there is slight vertical movement permitted by means of the plunger member which can move vertically within the recess 24, the projecting block 22 being smaller than the height of the housing hollow and accordingly provides a clearance 110. This clearance 110 permits the prosthesis containing the female section 14 to be pressed against the gum for the approximation of a feeling of elasticity of a living bone in the human mouth, so that the prosthesis, when inserted in the mouth, more nearly feels like natural teeth to the wearer. At the sme time, the holding device provides a secure engagement which prevents wobble and provides the necessary security to hold the dental prosthesis in place, wherein the plunger member 60 will seat itself in the recess 24 in the position shown in FIG. 3 when there is no applied pressure on the prosthesis.

The prosthesis can be removed by pulling upward on the prothesis. This upward pull will force the conical surface 72 of the forward end of the plunger member 60 to move inward of the casing 32 as it is pulled upward in the recess 24. The movement inwardly of the plunger member 60 releases the engagement between the male section 12 and the female section 14, and allows the dental prosthesis to be removed.

By means of the key 100 being retained in the keyway 92, there is provided a longer path of engagement for an improved securement of the male and female sections 12 and 14, which also accurately directs the two sections into the engagement positon. Thus, there is prevented any rotation between the male and female sections 12 and 14, where any lateral movement is also prevented between the male and female sections 12 and 14. In this manner, even though the two sections can be separated, when the removable prosthesis is properly positioned in the patient's mouth, it will be retained securely and will not rotate or provide any lateral displacement which could cause damage thereto or a feeling of insecurity to the user.

Figure 4:
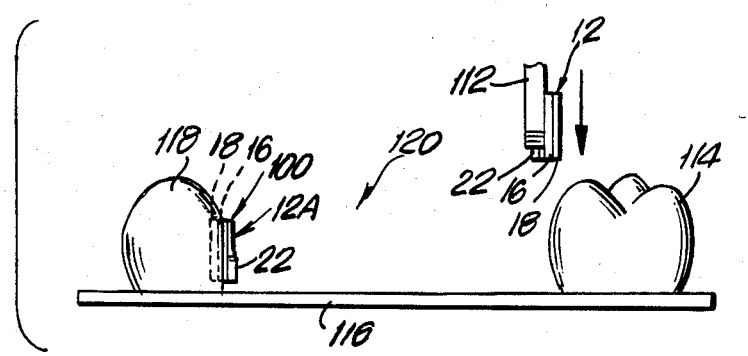
FIGS. 4 and 5 show steps in the placement of the retaining device when utilizing it in conjunction with a dental prosthesis.

In order to accurately position the male section, there can be utilized a jig similar to that described in the aforementioned U.S. Pat. No. 4,348,181. FIG. 4 shows the lower grasping arm portion 112 of such a jig which can be utilized with a suitable parallel tool in positioning the male section 12 in place in order to align it in parallelism with a corresponding male section 12A, such parallelism being well known in the dental art.

As shown in FIG. 4, the arm portion 112 of the jig (not shown) grasps the male section 12. With the male section securely held in the jig, the jig can be used to wax the male section 12 in place adjacent the cast tooth model 114 of the patient's teeth. Such cast model is formed by well known methods and is positioned in a holding plate 116. The corresponding male section 12A is shown waxed already in place on the cast tooth model 118. The male sections 12 and 12A are placed, by using the jig and parallel tool, so that they are parallel to each other. Crowns 124, 126 will then be cast in the usual manner from each of the teeth models 114, 118, including the male sections 12, 12A therein so that the male sections 12, 12A will be formed within each crown. It should be noted, that one projecting block 22 and key 100 will extend forward from the side of each crown 124, 126, as shown in FIG. 5.

Within the free space 120 between the male sections 12, 12A, there is formed a suitable dental prosthesis, in accordance with standard techniques. For example, as shown in FIG. 5, a bridge 122 has been formed for insertion between the existing teeth. It should be noted, that within the prosthesis 122 when cast, is included the female sections 14 and 14A which have been suitably positioned by attachment to the male sections 12, 12A, respectively, when the prosthesis 122 was being formed.

Figure 5:
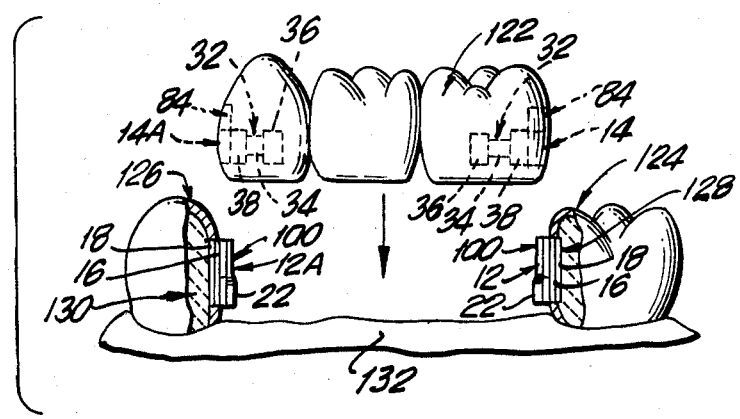

Once the crowns 124, 126 have suitably been cast from the teeth models 114, 118, the crowns are positioned in place on the actual teeth 128, 130, which have previously been prepared, as shown in FIG. 5. The male sections 12 and 12A will thus be secured directly to the actual teeth 128, 130 positioned in the mount. The dental prosthesis 122 can then be inserted onto the gum 132 and positioned between the existing teeth 128, 130 so that the female sections 14, 14A will lock onto the male sections 12, 12A as heretofore described.

Figure 6:
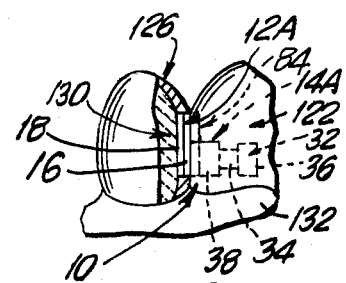
FIG. 6 is a partially broken away elevational view showing the positioning of the sections of the retaining device between the removable prosthesis and the fixed teeth in the mouth area.

Referring now to FIG. 6, there is shown in more detail the actual tooth 130 having the crown 126 thereon with the male section 12A engaging the female section 14A which in turn is secured into the portion of the dental prosthesis 122. It is noted, that the spline 18 of the male section functions to secure the male members in the crowns 124, 126, and the configuration of the casing 32 of the female section functions to secure the female members in the dental prosthesis 122.

More particularly, in placing the sections, the model is initially surveyed to determine the correct position of the male sections 12, 12A. The goal is to keep the male sectoins 12, 12A within the normal contour of the teeth yet maintain the maximum length. The male sections 12, 12A are then placed into the jig one at a time, the jig being secured to the conventional parallelometer. The male sections 12, 12A are then waxed within a recess in order to properly receive the female sections 14, 14A. The male sections 12, 12A are waxed into place while still being held in the parallelometer.

Conventionally, a Bard Parker blade is placed on top of the male section 12 or 12A being worked on. The jig is then removed while counteracting the friction force with opposite pressure on the Bard Parker blade to prevent dislodging of the male section 12 or 12A being worked on. The waxing of the male sections 12, 12A are then completed to proper contour.

The casting is then processed in the conventional manner including the steps of providing the sprue and investing. The investment is then burnt out and the cast of the crown is made. When the crown is complete with the male sections 12 and 12A in place, the female sections 14, 14A are inserted into the male sections 12, 12A and the two sections secured together. An impression of the entire master model is taken and the denture casting or prosthesis 122 is constructed in the conventional manner. The dental casting 122 is then placed on the master model and secured to the back portion of the female sections 14, 14A either with plaster or wax. This procedure is used in order to obtain the proper relationship for soldering the denture casting 122 to the female sections 14, 14A.

It is noted, that should the plunger member 60 of the female section 14 fail to function properly, the plunger member 60 can be removed from the female section 14 without removing the female section 14 from the prosthesis 122. Accordingly, the bight of the U-shaped clip 78 is first located or found in the prosthesis 122, and the clip 78 is then removed from the female section 14 by pulling on the bight thereof. Once the clip 78 is removed, the plunger member 60 can be removed from the bore 58. Thus, the plunger member 60 and the spring 76 can be replaced in the female section 14. The new plunger member 60 is first held in the bore 58 and the clip 78 is then reinserted into the holes 80, 82. One of the legs of the clip 78 is longer than the other, so that the longer leg is first inserted into one of the holes 80, 82 to act as a guide for inserting the shorter leg into the other hole. The hole, which was made in the prosthesis 122 in order to locate the clip 78, is then filled in, in a conventional manner well known in the art.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A device for retaining a removable dental prosthesis comprising, in combination:
    a first member for securement to a fixed tooth, a projection extending from said first member;
    a second member for securement within the dental prosthesis, a housing extending from said second member for receiving said projection;
    retaining means for releasably retaining said projection within said housing; and
    engaging to prevent relative rotation and lateral movement between said first and second members, said engaging means including members extending from said hosuing and said projection for coacting with each other in an extended path of engagement to maintain stability between said first and second members;
    said members of said engaging means including a channel member upstanding from said housing, and a plug member upstanding from said projection and being slidably receivable within said channel member;
    said channel member including an internal longitudinal keyway having an open longitudinal mouth, and said plug member including an elongated key having a T-shaped cross sectional configuration defining a first transverse leg and a second perpendicular leg, said key being received in said keyway.

2. A device as in claim 1, wherein said first member includes a back plate, said projections being supported on a lower part of said back plate, and said key being supported on an upper part of said back plate with said perpendicular leg extending from said back plate and the transverse leg being spaced from and parallel to said back plate.

3. A device as in claim 1, wherein said retaining means includes a spring biased plunger member disposed in said second member and projecting into a hollow of said housing, a recess provided in said projection for receiving and retaining said plunger member therein, and wherein said transverse leg includes a concave groove to slidably accomodate said plunger member to direct it towards said recess.

4. A device as in claim 3, wherein said projection further includes a cam surface vertically positioned between said recess and said concave groove for guiding said plunger member into said recess.

5. A device as in claim 1, wherein said housing has substantially an inverted U-shape, and said internal keyway is in communication with an inside hollow of said housing, so that said housing can vertically receive said key which then enters said keyway as said housing vertically slides over said projection.

6. A device as in claim 5, wherein said projection includes vertical undercuts provided on opposite sides thereof for coacting with vertical undercut portions within said hollow of said housing to provide a tongue and groove engagement therebetween to provide additional engaging means to prevent relative rotation between said first and second members.

7. A retaining device for removably securing a dental prosthesis in opsition, said device comprising, in combination:
    a male section for securement to a side of a fixed tooth, and a cooperating female section for securement within the dental prosthesis;
    said female section including an elongated casing, said male section including a projecting member receivable in said casing;

a spring loaded plunger disposed in said casing, said plunger having a projecting portion, stop means within said casing for limiting extent of longitudinal travel of said plunger;

said male section including securing means for fixedly retaining said male section in place on the fixed tooth;

said projecting member including a recess for cooperatively receiving said projecting portion of said plunger to thereby anchor the dentral prosthesis to the fixed tooth; and engaging means coacting between said male and female sections to prevent relative rotation and lateral movement between said male and femal sections, said engaging means including elongated members extending from said casing and said projecting member for engaging with each other in an extended path of engagement to maintain stability between said male and female sections;

said elongated members of said engaging means including a channel member upstanding from said casing, and a plug member extending from said projecting member and being slidably receivable within said channel member;

said channel member including an internal longitudinal keyway having an open longitudinal mouth, and said plug member including an elongated key having a T-shaped cross sectional configuration defining a first transverse leg and a second perpendicular leg, said key being received in said keyway.

8. A retaining device as in claim 7, wherein the transverse leg includes a concave groove to slidably accommodate said projecting portion of said plunger for guiding said plunger into said recess of said projecting member.

9. A retaining device as in claim 7, wherein said internal keyway is in communication with an inside hollow of said casing so that said casing can vertically receive said key which then enters said key way as said casing vertically slides over said projection.

10. A retaining device as in claim 7, wherein said male section includes a plate, said projecting member extending from a lower portion of one side of said plate, and said perpendicular leg extending from an upper portion of said one side of said plate, said securing means including a dovetailed spline extending from an opposite side of said plate.

11. A retaining device as in claim 8, wherein said projecting member includes a cam surface vertically positioned between said recess and said concave groove for guiding said plunger into said recess of said projecting member.

12. A retaining device for removably securing a dental prosthesis in position, said device comprising, in combination:

a male section for securement to a side of a fixed tooth, and a cooperating female section for securement within the dental prosthesis;

said female section including an elongated casing, said male section including a projecting member receivable in said casing;

a spring loaded plunger disposed in said casing, said plunger having a projecting portion, stop means within said casing for limiting extent of longitudinal travel of said plunger;

said male section including securing means for fixedly retaining said male section in place on the fixed tooth;

said projecting member including a recess for cooperatively receiving said projecting portion of said plunger to thereby anchor the dental prosthesis to the fixed tooth;

engaging means coacting between said male and female sections to prevent relative rotation and lateral movement between said male and female sections, said engaging means including elongated members extending from said casing and said projecting member for engaging with each other in an extended path of engagement to maintain stability between said male and female sections;

a plunger including an elongated cylindrical body portion;

longitudinally spaced apart enlarged collars being provided on said body portion to define a neck portion therebetween; and said stop means including a restricting member in said casing adjacent said neck portion for engaging said collars to capture said plunger member within said casing and to limit its longitudinal movement.

13. A retaining device as in claim 12, wherein said restricting member includes a wire clip removably inserted through a wall of said casing.

14. A retaining device as in claim 12, wherein said casing includes a body portion, an enlarged foot portion at one end thereof for assisting in securement of said casing within the dental prosthesis, and a forward head portion at an opposite end of said casing, said forward head portion having flat sides thereabout to prevent rotation within the dental prosthesis.

15. A retaining device as in claim 12, wherein said casing includes a forward head portion having an inverted U-shaped housing for receiving said projecting member of said male section therein, internal side walls of said housing and external side walls of said projecting member being undercut to provide a tongue and groove engagement therebetween for preventing relative rotation.

16. A retaining device for removably securing a dental prosthesis in position, said device comprising, in combination:

a male section for securement to a side of a fixed tooth, and a cooperating female section for securement within the dental prosthesis;

said female section including an elongated casing, said male section including a projecting member receivable in said casing;

a spring loaded plunger disposed in said casing, said plunger having a projecting portion, stop means within said casing for limiting extent of longitudinal travel of said plunger;

said male section including securing means for fixedly retaining said male section in place on the fixed tooth;

said projecting member including a recess for cooperatively receiving said projecting portion of said plunger to thereby anchor the dental prosthesis to the fixed tooth;

engaging means coacting between said male and female sections to prevent relative rotation and lateral movement between said male and female sections, said engaging means including elongated members extending from said casing and said projecting member for engaging with each other in an extended path of engagement to maintain stability between said male and female sections; and vertical undercuts being laterally provided in opposite sides of said projecting member to receive vertical undercut portions provided in said casing to define a tongue and groove engagement therebetween for preventing relative rotation.

* * * * *